United States Patent

Andersson et al.

[11] Patent Number: 4,612,316
[45] Date of Patent: Sep. 16, 1986

[54] TRICYCLIC AMINES WITH CENTRAL DOPAMINERGIC ACTIVITY

[75] Inventors: Bengt R. Andersson, Mölndal; Folke L. Arvidsson, Upsala; Per A. E. Carlsson; John S. M. Hjort, both of Gothenburg; Anette M. Johansson, Upsala; Per L. Lindberg, Askim; John L. G. Nilsson, Tullinge; Domingo Sanchez, Floda; Kjell A. I. Svensson, Gothenburg; Hakan V. Wikström, Partille, all of Sweden

[73] Assignee: Astra Lakemedel Aktiebolag, Sodertalje, Sweden

[21] Appl. No.: 601,981

[22] Filed: Apr. 19, 1984

[30] Foreign Application Priority Data

Apr. 27, 1983 [SE] Sweden ................ 8302361

[51] Int. Cl.⁴ .................. A61K 31/445; C07D 221/10
[52] U.S. Cl. .................... 514/290; 540/101; 540/110
[58] Field of Search ............ 546/110, 101; 424/256; 514/290

[56] References Cited

U.S. PATENT DOCUMENTS 2,525,502 10/1950 Tulagin et al. ................ 546/101
4,341,786  7/1982 DeMarinis et al. ............ 546/101

FOREIGN PATENT DOCUMENTS 0059553  9/1982 European Pat. Off. .......... 546/79
2044172  3/1971 Fed. Rep. of Germany ...... 548/450
4741900  3/1970 Japan ............................ 546/101
1277789  6/1972 United Kingdom ............. 548/450
1596170  8/1981 United Kingdom ............. 546/79

OTHER PUBLICATIONS

Cannon, et al., *Journal of Medicinal Chemistry*, 1976, 19(8), pp. 987-993.
Van Oene, et al., 99:64108t, *Chemical Abstracts*, (1982).
Wikstrom, et al, *Journal of Medicinal Chemistry*, 1982, 25(8), pp. 925-931.
Van Oene, J., et al., *Eur. J. Pharmacol.*, 87 (1983), 491-495.
Cannon, J., et al., *Journal of Medicinal Chemistry*, 1979, 22(4), pp. 341-347.
Cannon, J., et al., *Journal of Medicinal Chemistry*, 1976, 19(8), pp. 987-993.
Cannon, J., et al., *Journal of Medicinal Chemistry*, 1980, 23(1), pp. 1-5.
*Chemical Abstracts*, vol. 92 (1980), abstract No. 51846n, [*J. Med. Chem.*, 1980, 23(1), 1-5].
*Chemical Abstracts*, vol. 86 (1977), abstract No. 37497u, [*J. Pharmacol. Exp. Ther.*, 1976, 199(3), 630-8].

*Primary Examiner*—Richard A. Schwartz

[57] ABSTRACT

Compounds of the formula

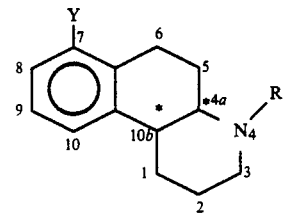

wherein $C^1$ and $N^4$ are in trans configuration to each other, wherein R and Y are defined herein below, as bases and pharmaceutically acceptable acid addition salts thereof, processes for their preparation and pharmaceutical preparations and methods of treatment employing such compounds. The compounds are useful for treatment of disorders in the central nervous system.

8 Claims, No Drawings

TRICYCLIC AMINES WITH CENTRAL DOPAMINERGIC ACTIVITY

TECHNICAL FIELD

The present invention is related to new substituted octahydrobenzo(f)quinolines, to processes for preparing such compounds as well as to pharmaceutical preparations thereof and methods of treatment employing such compounds.

An object of the invention is to provide compounds for therapeutic use, especially having a therapeutic activity in the central nervous system.

BACKGROUND ART

Compounds of the formula

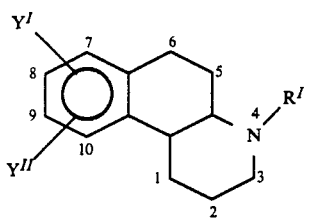

are disclosed by a number of references. Thus, Cannon et al. (J. Med. Chem. 19, 987 (1976)) describe i.a. compounds wherein $R^I$ is $CH_3$ and $Y^I$ and $Y^{II}$ are both H, $Y^I$ is 7—OH (or 7—OCH$_3$) and $Y^{II}$ is H, or $Y^I$ is 8—OH (or 8—OCH$_3$) and $Y^{II}$ is H, or $Y^I$ is 7—OH (or 7—OCH$_3$) and $Y^{II}$ is 8—OH (or 8—OCH$_3$). Further, compounds wherein $R^I$ is H, $C_2H_5$, n—$C_3H_7$ or benzyl and $Y^I$ is 7—OH (or 7—OCH$_3$) and $Y^{II}$ is 8—OH (or 8—OCH$_3$), respectively, have been described by Cannon et al. (J. Med. Chem. 22, 341 (1979)). Said compounds are indicated to have central dopaminergic properties although the monohydroxy compounds are reported to be only weakly active and the non-hydroxy compound to be inactive.

Cannon et al. (J. Med. Chem. 23, 1 (1980)) also describe compounds wherein $Y^I$ is 8—OH (or 8—OCH$_3$), $Y^{II}$ is 9—OH (or 9—OCH$_3$) and $R^I$ is H, CH$_3$, $C_2H_5$ or n—$C_3H_7$. Said compounds are claimed to be inactive in the central nervous system but to be potent dopamine agonists in the periphery.

Wikström et al. (J. Med. Chem., 1982, 25, 925-931) describe compounds under the above formula wherein $Y^{II}$ is H, $Y^I$ is 7—OH, 8—OH, 9—OH and 10—OH and $R^I$ is n—Pr and n—Bu having dopaminergic properties. However, these compounds stimulate both presynaptic and postsynaptic dopamine receptors. The hydroxy compounds mentioned were prepared by demethylating the corresponding methoxy compounds. In the preparation of those methoxy compounds, intermediates are employed wherein $Y^{II}$ is H, $Y^I$ is CH$_3$O and $R^I$ is H.

DE Offenlegungsschrift No. 20 44 172 describes compounds under the formula

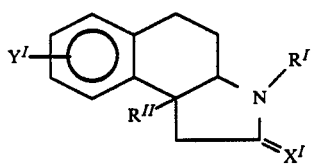

wherein $R^I$ and $R^{II}$ represent H or alkyl, $X^I$ represents $H_2$ or O and $Y^I$ represents H, alkoxy or hydroxy. Said compounds are claimed to have analgesic activity.

DISCLOSURE OF INVENTION

According to the present invention it has been found that novel compounds of the formula

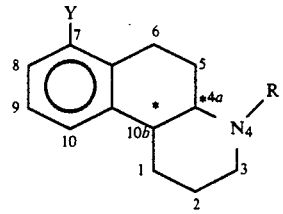

I wherein $C^1$ and $N^4$ are in trans configuration to each other, Y is OH, $R^1COO$, $R^2R^3NCOO$— or $R^4O$ whereby $R^1$ is an aliphatic hydrocarbon residue having 1-17 carbon atoms, a phenyl, 2,6-dimethylphenyl or 3- or 4-hydroxyphenyl group or a 3- or 4-alkanoyloxyphenyl group with the formula

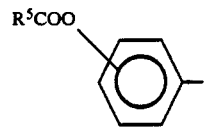

wherein $R^5$ is an alkyl group having 1-6 carbon atoms, or $R^1$ is a group

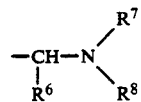

wherein $R^6$ is hydrogen, an alkyl group having 1 to 5 carbon atoms or a phenyl group, $R^7$ is hydrogen, an alkyl group having 1 to 5 carbon atoms or an acyl group, preferably an acyl group having 2 to 7 carbon atoms, and $R^8$ is hydrogen or an alkyl group having 1 to 5 carbon atoms, $R^2$ is hydrogen, an alkyl group having 1-5 carbon atoms, a phenethyl, benzyl or phenyl group which may be mono- or disubstituted in the aromatic part with a methyl, methoxy, hydroxy, nitro or cyano group or a halogen, $R^3$ is H, an alkyl group having 1 to 5 carbon atoms or a phenyl group or $R^2$ and $R^3$ together with the nitrogen atom form a 5, 6 or 7 membered ring that may contain 1 to 3 double bonds and/or 1 to 2 further heteroatoms selected from N, O and S, and $R^4$ is an allyl or benzyl group and R is hydrogen or the group

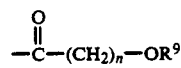

wherein n is 3 or 4 and $R^9$ is hydrogen, an alkanoyl group having 2-6 carbon atoms or benzoyl, as bases and pharmaceutically acceptable acid addition salts thereof, are potent neuropharmacological agents. Thus, said compounds are active as selective presynaptic dopamine receptor agonists when administered to animals including man. The compounds are thus useful for treatment of disorders in the central nervous system especially psychotic disorders in man.

An alkyl group may be a straight alkyl group or a branched alkyl group having at least 3 carbon atoms.

Symbols for numbers, atoms or groups referred to below have the broadest meaning previously assigned unless specified otherwise.

Both organic and inorganic acids can be employed to form non-toxic pharmaceutically acceptable acid addition salts of the compounds of this invention. Illustrative acids are sulfuric, nitric, phosphoric, hydrochloric, citric, acetic, lactic, tartaric, pamoic, ethanedisulfonic, sulfamic, succinic, cyclohexylsulfamic, fumaric, maleic and benzoic acid. These salts are readily prepared by methods known in the art.

In a preferred embodiment the invention is related to compounds of the formula I above wherein Y is OH, $R^1COO$, or $R^2R^3NCOO-$, whereby $R^1$ is an alkyl group having 1-5 carbon atoms, or a phenyl group, and $R^2$ is an alkyl group having 1-5 carbon atoms, a phenethyl, benzyl or phenyl group, and $R^3$ is H or an alkyl group having 1-5 carbon atoms.

One group of preferred compounds are those wherein Y is OH or $R^2R^3NCOO$. Further preferred are compounds wherein R is H or 4-hydroxybutyryl.

Preferred compounds are those wherein Y is OH and R is H or 4-hydroxybutyryl.

The compounds of formula I contain two asymmetric carbon atoms in the aliphatic moiety as indicated by asterisks in the above formula. The therapeutic properties of the compounds are ascribed to the trans isomers. The pure enantiomers as well as mixtures thereof are within the scope of the invention. The preferred enantiomers are those with 4aS,10bS-configuration.

The invention takes into consideration that compounds which structurally deviate from the formula I, after administration to a living organism may be transformed to compounds of the formula I and in this structural form exert their effect. This consideration is a further aspect of the invention. Likewise, certain compounds of formula I may be metabolized into other compounds of formula I before exerting their effect. Compounds of the invention as defined above wherein Y is other than hydroxy and compounds wherein R is other than hydrogen are thus believed to exert their main activity after metabolism to compounds wherein Y is hydroxy and R is hydrogen, respectively.

Methods of Preparation

The compounds of the invention may be obtained by one of the following methods constituting a further aspect of the invention.

(a) An ether or ester of the formula

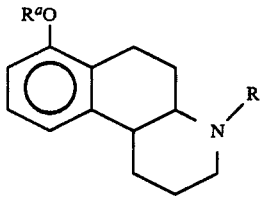

II wherein $R^a$ represents a hydrocarbon residue, preferably an alkyl group having 1-5 carbon atoms, or a benzyl group, and R is as defined above, may be cleaved to form a compound of formula I wherein Y is a hydroxy group.

The cleavage may be carried out by treating the compound of formula II with an acidic nucleophilic reagent such as aqueous HBr, or HI, $HBr/CH_3COOH$, $BBr_3$, $AlCl_3$, pyridine-HCl or $(CH_3)_3SiI$, or with a basic nucleophilic reagent such as $CH_3C_6H_4-S^\ominus$ or $C_2H_5-S^\ominus$. When $R^a$ is a benzyl group the cleavage may also be carried out by reduction, preferably with hydrogen using Pd or $PtO_2$ as catalyst.

A compound of formula II wherein $R^a$ is a methyl group is obtained from a compound of formula IIA, as described in J. Med. Chem. 1982, 25, 925. Compounds of formula II wherein $R^a$ is an alkyl group with 2-5 carbon atoms are synthesized in an analogous manner starting from the appropriately substituted compound IIA.

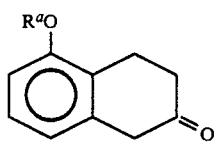

IIA (b) A compound of formula

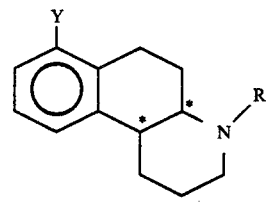

I wherein Y is OH and R is as defined above may be converted into a compound of the formula I wherein Y is $R^1COO$, $R^2R^3NCOO$ or $R^4O$ by treating the first mentioned compound with an appropriate carboxylic acid halide $R^1COX$ or anhydride $(R^1CO)_2O$ or with an appropriate carbamoyl halide $R^2R^3NCOX$ in the presence of a base (only when R is other than hydrogen) such as triethylamine or pyridine or an acid such as $H_2SO_4$ or $CF_3COOH$ or with an appropriate allyl, benzyl or methyl halide $R^4X$ in the presence of a base such as triethylamine, pyridine or potassium t-butoxide. X represents a halogen, preferably Cl or Br.

Alternatively, when conversion of Y=OH into $R^1COO$ is intended and $R^1$ is

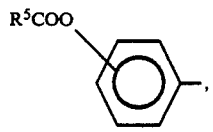

a compound of formula I wherein Y is OH may first be converted to a compound of formula I wherein Y is

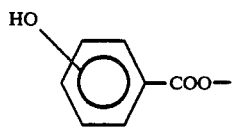

which is then treated with an appropriate carboxylic acid halide R⁵COX or anhydride (R⁵CO)₂O in the presence of a base or an acid.

(c) A compound of the formula

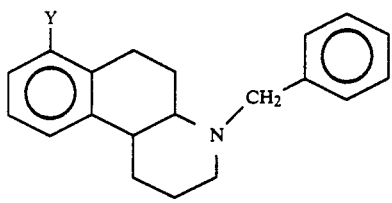
IV wherein Y is other than allyloxy, may be hydrogenated to form a compound of formula I wherein R is H. The hydrogenation is carried out in the presence of a catalyst such as Pd. The starting material of formula IV is obtained by demethylation of the corresponding methoxy compound described in J. Med. Chem. 1982, 25, 925–931, and, when Y other than OH is required, subsequent acylation in analogy with (b) above.

(d) An amide of the formula

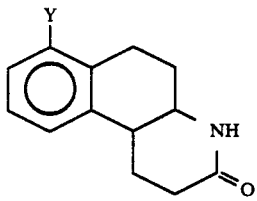
V wherein Y is other than R²R³NCOO, may be converted into a compound of the formula I by reduction of the amide function and the ester function R¹COO if present. Thus the compound of formula V may be treated with a reducing agent preferably a hydride reducing agent such as LiAlH₄ or BH₃ in an ethereal solvent or a metal reducing agent such as Na in an alcoholic solvent such as n-butanol. When an ester function is present this is converted to a hydroxy group.

(e) A compound according to the formula

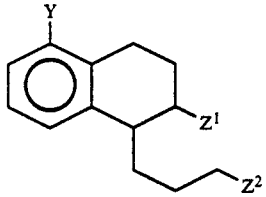
VI wherein one of the groups Z¹ and Z² is a leaving group X and the other is NH₂, or Z¹ and Z² are both leaving groups X, and X is a leaving group such as Cl, Br, I or —OSO₂C₆H₄CH₃, may be converted to a compound of formula I wherein Y is as defined above and R is H, by treating the compound of formula VI, or when one of Z¹ and Z² is NH₂, an acid addition salt thereof, with a base such as (C₂H₅)₃N or K₂CO₃, whereby the compound of formula VI is treated together with an equivalent amount of ammonia or an acid addition salt thereof when Z₁ and Z² are both X. The conversion is carried out in a solvent such as tetrahydrofuran, dioxan or acetonitrile, if necessary with simultaneous or subsequent heating of the mixture.

(f) A carbonyl-containing compound of the formula

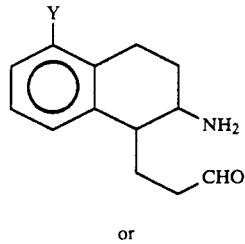
VII or

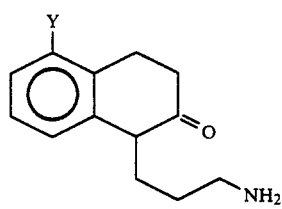
VIII wherein Y is other than allyloxy, may be subjected to an intramolecular reductive alkylation, preferably by using catalytic hydrogenation, to give a compound of the formula I wherein R is hydrogen. When Y is benzyloxy this is converted to OH.

(g) In a compound of the formula

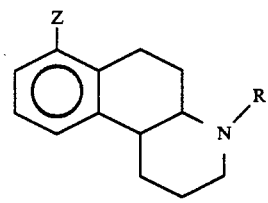
IX wherein Z represents SO₃H, Cl or NH₂, a hydroxy group may be substituted for the group Z to the formation of a compound of formula I wherein Y represents a hydroxy group. When Z is SO₃H or Cl said reaction may be carried out by treatment with a strong alkali under heating, suitably with an alkali melt such as KOH when Z is SO₃H, and with a strong aqueous alkali such as NaOH or KOH when Z is Cl. When Z is NH₂ the reaction may be carried out by treatment with aqueous nitrous acid to the formation of an intermediate diazonium compound which is then subjected to hydrolysis in water.

(h) A racemic mixture or a mixture partly enriched on one of the enantiomers of a compound of formula

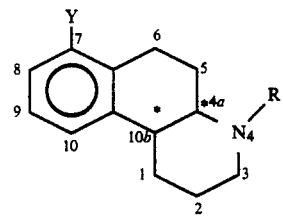
I may be subjected to enantiomeric separation to obtain the desired enantiomer of compound I. This may be done by methods known in the art. These methods include recrystallization of diastereomeric salts with pure enantiomers of acids such as tartaric acid, O,O'-dibenzoyltartaric acid, mandelic acid and camphor-10-sulphonic acid.

Free bases formed may subsequently be converted into their acid addition salts, and acid addition salts formed may subsequently be converted into the corresponding bases or other acid addition salts.

Pharmaceutical Preparations

Pharmaceutical preparations of the compounds of the invention constitute a further aspect of the invention.

In clinical practice the compounds of the present invention will normally be administered orally, rectally, or by injection, in the form of pharmaceutical preparations comprising the active ingredient either as a free base or as a pharmaceutically acceptable non-toxic, acid addition salt, e.g. the hydrochloride, lactate, acetate, sulfamate, and the like, in association with a pharmaceutically acceptable carrier.

Accordingly, terms relating to the novel compounds of this invention, whether generically or specifically, are intended to include both the free amine base and the acid addition salts of the free base, unless the context in which such terms are used, e.g. in the specific examples, would be inconsistent with the broad concept. The carrier may be a solid, semisolid or liquid diluent or capsule. These pharmaceutical preparations constitute a further aspect of this invention. Usually the active substance will constitute between 0.1 and 99% by weight of the preparation, more specifically between 0.5 and 20% by weight for preparations intended for injection and between 0.2 and 95% by weight for preparations suitable for oral administration.

Pharmaceutical preparations containing a compound of the invention in a solid form of dosage units for oral application may preferably contain between 2 and 95% by weight of the active substance, in such preparations the selected compound may be mixed with a solid fine grain carrier, e.g. lactose, saccharose, sorbitol, mannitol, starches such as potato starch, corn starch or amylopectin, cellulose derivatives, or gelatin and a lubricant such as magnesium stearate, calcium stearate, polyethylene glycol waxes, and the like, and then compressed to form tablets. If coated tablets are required, the cores, prepared as described above, may be coated with a concentrated sugar solution which may contain, e.g. gum arabic, gelatin, talcum, titanium dioxide, and the like. Alternatively, the tablet can be coated with a lacquer dissolved in a readily volatile organic solvent or mixture of organic solvents. Dyestuffs may be added to these coatings in order to readily distinguish between tablets containing different active substances or different amounts of the active compound.

For the preparation of soft gelatin capsules (pearl-shaped closed capsules) consisting of gelatin and, for example, glycerol, or similar closed capsules, the active substance may be admixed with a vegetable oil. Hard gelatin capsules may contain granulates of the active substance in combination with solid, fine grain carriers such as lactose, saccharose, sorbitol, mannitol, starches (e.g. potato starch, corn starch or amylopectin), cellulose derivatives or gelatin.

Liquid preparations for oral application may be in the form of syrups or suspensions, for example, solutions containing from about 0.2% to about 20% by weight of the active substance herein described, the balance being sugar and a mixture of ethanol, water, glycerol and propylene glycol. Optionally such liquid preparations may contain colouring agents, flavouring agents, saccharine and carboxymethylcellulose as a thickening agent.

Solutions for parenteral applications by injection can be prepared in an aqueous solution of a water-soluble pharmaceutically acceptable salt of the active substance preferably in a concentration of from about 0.5% to about 10% by weight. These solutions may also contain stabilizing agents and/or buffering agents and may conveniently be provided in various dosage unit ampoules.

In therapeutical treatment the suitable daily doses of the compounds of the invention are 50–10000 mg for oral application, preferentially 200–5000 mg, and 0.005–500 mg for parenteral application, preferentially 0.25–250 mg.

Working Examples

The following examples will further illustrate the invention.

Preparation of Intermediates

EXAMPLE I1

(+)-trans-(4aR,10bR)- and (−)-trans-(4aS,10bS)-7-methoxy-1,2,3,4,4a,5,6,10b-octahydrobenzo(f)quinoline hydrochloride (Method h)

Trans-7-methoxy-1,2,3,4,4a,5,6,10b-octahydrobenzo(f)quinoline hydrochloride (0.50 g, 2.0 mmol), R(−)-O-methylmandelic acid chloride (0.36 g, 2.2 mmol), methylene chloride (10 ml), water (10 ml) and 5% NaOH (10 ml) were mixed and stirred for 5 min. Extraction with ether, drying and evaporation of the volatiles gave an oil (0.77 g, theoretically 0.72 g). When adding ether to this oil, crystals of isomer 1 melting at 151°–153° C. were precipitated out (0.20 g, 28%), optical purity according to HPLC 96.3%. After three additional crystallizations giving an additional 0.13 g of isomer 1 the mother liquor was concentrated to an oil (0.26 g). The oil (0.26 g) was chromatographically separated by repeated injections to a semi-preparative HPLC column (SiO$_2$) using hexane-ethyl acetate-ethanol (95.5:3.75:0.75) as the motile phase giving isomer 2 (0.16 g) (98.2% of isomer 2 and 1.8% of isomer 1).

Isomer 1 (0.19 g, 0.52 mmol) was dissolved in dry THF (40 ml) and treated with potassium tert. butoxide (0.81 g, 7.1 mmol) and H$_2$O (64 μl, 3.6 mmol) and the mixture was stirred overnight and then refluxed for 1 hour. Water was added and the mixture was extracted with ether. The organic layer was dried and the solvent evaporated. The residue was treated with HCl/EtOH, evaporated and recrystallized from ethanol/ether to give the desired (+)-trans-(4aR;10bR) product (120 mg, 87% on the resolved amide isomer 1), m.p. 296°–301° C., $[\alpha]_D^{22}$ +81° (c0.96, MeOH).

Isomer 2 (0.16 g; 0.44 mmol) was dissolved in dry THF (20 ml) and treated with potassium tert. butoxide (0.81 g, 7.1 mmol) and H$_2$O (64 μl, 3.6 mmol) and the mixture was stirred overnight. The mixture was then refluxed for 1 hour. Water was added and the mixture was extracted with ether. The organic layer was dried and the solvent evaporated. The residue was converted to its hydrochloride, evaporated and recrystallized (ethanol-ether) giving 55 mg (50% on the resolved amide isomer 2) of the desired (−)-trans-(4aS;10bS) product, m.p. 296°–301° C., $[\alpha]_D$ > −88° (c 1.05, MeOH).

EXAMPLE I2

(+)-trans-7-methoxy-4-hydroxybutyryl-1,2,3,4,4a,5,6,10b-octahydrobenzo(f)quinoline (±)-trans-7-methoxy-1,2,3,4,4a,5,6,10b-octahydrobenzo(f)-quinoline hydrochloride (0.50 g, 1.9 mmol) was converted to the free base by partitioning between $CH_2Cl_2$ and 10% $Na_2CO_3$. Drying and evaporation of volatiles gave an oil which was mixed with γ-butyrolactone (0.33 g, 3.8 mmol) and 2-hydroxypyridine (0.36 g, 3.8 mmol) and dry toluene (2 ml). The mixture was refluxed for 25 hours. After one night at room temperature the precipitate (2-hydroxypyridine) was filtered off, the filtrate extracted with $H_2O/CH_2Cl_2$, the organic layer washed with 0.5M HCl, dried and evaporated giving an oil. This was purified on a $SiO_2$-column using ethyl acetate as eluant, giving 0.25 g (46%) of the desired product.

EXAMPLE I3
(±)-trans-7-Phenylcarbamoyloxy-4-benzyl-1,2,3,4,4a,5,6,10b-octahydrobenzo(f)quinoline hydrobromide (±)-trans-7-Methoxy-4-benzyl-1,2,3,4,4a,5,6,10b-octahydro(f)quinoline hydrochloride (50 mg, 0.15 mmol) was heated in 48% HBr for 2 hours at 125° C. under nitrogen. The hydrobromic acid was evaporated off and the residue alkalized ($Na_2CO_3$) and extracted with ethyl acetate. Evaporation of the solvent yielded an oil which was dissolved in toluene and refluxed in the presence of phenyl isocyanate (18 mg) for three hours. Extractive work up gave the product (40 mg) as an oil which was debenzylated as described in Example E6.

Preparation of end compounds

EXAMPLE E1
(±)-trans-7-Hydroxy-1,2,3,4,4a,5,6,10b-octahydrobenzo(f)quinoline hydrobromide (Method a)

(±)-trans-7-Methoxy-1,2,3,4,4a,5,6,10b-octahydrobenzo(f)quinoline (0.40 g, 1.8 mmol) was refluxed in 48% aqueous HBr under $N_2$ (g) for two hours. The acid was evaporated and the residue was recrystallized from MeOH-ether giving the desired product (0.39 g, 90%), m.p. 320°–330° C. (dec.).

EXAMPLE E2
(−)-trans-(4aS;10bS)-7-Hydroxy-1,2,3,4,4a,5,6,10b-octahydrobenzo(f)quinoline hydrobromide (Method a)

(−)-trans-(4aS,10bS)-7-Methoxy-1,2,3,4,4a,5,6,10b-octahydrobenzo(f)quinoline hydrochloride (50 mg, 0.20 mmol) was heated in 48% aqueous HBr for 2 hours at 125° C. under nitrogen. The hydrobromic acid was evaporated off and the residue was recrystallized from MeOH-ether yielding the desired product (59 mg, 92%), 100% optical purity according to HPLC, m.p. 320°–330° C. (dec.), $[\alpha]_D^{22}$ −60° (c 0.5, MeOH), GC-MS: $M^+ = m/e = 203$.

EXAMPLE E3
(+)-trans-(4aR;10bR)-7-Hydroxy-1,2,3,4,4a,5,6,10b-octahydrobenzo(f)quinoline hydrobromide (Method a)

(+)-trans-(4aR;10bR)-7-Methoxy-1,2,3,4,4a,5,6,10b-octahydrobenzo(f)quinoline hydrochloride (0.12 g, 0.47 mmol) was heated in 48% aqueous HBr for 2 hours at 125° C. under nitrogen. The hydrobromic acid was evaporated off and the residue was recrystallized from MeOH-ether yielding the desired product (0.11 g, 85%), 100% optical purity according to HPLC, m.p. 320°–330° C. (dec.), $[\alpha]_D^{22}$ +60° (c 0.5, MeOH), GC-MS: $M^+ = m/e = 203$.

EXAMPLE E4
(±)-trans-7-Hydroxy-4-hydroxybutyryl-1,2,3,4,4a,5,6,10b-octahydrobenzo(f)quinoline. (Method a)

(±)-trans-7-Methoxy-4-hydroxybutyryl-1,2,3,4,4a,5,6,10b-octahydrobenzo(f)quinoline (0.25 g, 0.88 mmol) was dissolved in $CH_2Cl_2$ (15 ml) and the solution was chilled to −70° C. $BBr_3$ (0.7 ml) was added at this temperature. The mixture was allowed to reach room temperature under stirring. The reaction was quenched with water. The mixture was extracted with ether. The organic layer was dried and the solvent evaporated giving the desired product (0.16 g, 68%).

EXAMPLE E5
(±)-trans-7-Pivaloyloxy-1,2,3,4,4a,5,6,10b-octahydrobenzo(f)quinoline hydrobromide (Method b)

(±)-trans-7-Hydroxy-1,2,3,4,4a,5,6,10b-octahydrobenzo(f)quinoline hydrobromide (50 mg, 0.17 mmol) was dissolved in trifluoroacetic acid (1 ml). Pivaloyl chloride (0.2 ml) was added and the mixture was stirred at room temperature overnight. After evaporation of the solvent, the residue was partitioned between $H_2O$ and $CH_2Cl_2$. The organic layer was concentrated and applied to a $SiO_2$ column and the product was eluted with $CH_2Cl_2$-MeOH. Fractions containing the product were collected. The solvent was evaporated yielding 20 mg of an oil. GC-MS: $M^+$ at m/e 287.

EXAMPLE E6
(±)-trans-7-Phenylcarbamoyloxy-1,2,3,4,4a,5,6,10b-octahydrobenzo(f)quinoline hydrochloride (Method c)

(±)-trans-7-Phenylcarbamoyloxy-4-benzyl-1,2,3,4,4a,5,6,10b-Octahydrobenzo(f)quinoline hydrochloride (40 mg, 0.12 mmol) was dissolved in MeOH (5 ml) and hydrogenolyzed in the presence of 10% Pd/C (40 mg) at 25 psig at room temperature. After filtration of the catalyst and evaporation of the solvent the desired product (20 mg) was obtained. MS shows $M^+$ at m/e 322.

Pharmaceutical Preparations

The following examples illustrate how the compounds of the present invention may be included into pharmaceutical preparations.

EXAMPLE P1. PREPARATION OF SOFT GELATINE CAPSULES 500 g of active substance are mixed with 500 g of corn oil, whereupon the mixture is filled in soft gelatine capsules, each capsule containing 100 mg of the mixture (i.e. 50 mg of active substance).

EXAMPLE P2. PREPARATION OF TABLETS 0.5 kg of active substance are mixed with 0.2 kg of silicic acid of the trade mark Aerosil. 0.45 kg of potato starch and 0.5 kg of lactose are mixed therewith and the mixture is moistened with a starch paste prepared from 50 g of potato starch and distilled water, whereupon the mixture is granulated through a sieve. The granulate is dried and sieved, whereupon 20 g of magnesium stearate are mixed into it. Finally the mixture is pressed into tablets each weighing 172 mg.

EXAMPLE P3. PREPARATION OF A SYRUP 100 g of active substance are dissolved in 300 g of 95% ethanol, whereupon 300 g of glycerol, aroma and colouring agents (q.s.) and 1000 ml of water are mixed therein. A syrup is obtained.

EXAMPLE P4. PREPARATION OF AN INJECTION SOLUTION

Active substance (hydrobromide) (1 g), sodium chloride (0.8 g) and ascorbic acid (0.1 g) are dissolved in sufficient amount of distilled water to give 100 ml of solution. This solution, which contains 10 mg of active substance per ml, is used in filling ampoules, which are sterilized by heating at 120° C. for 20 minutes.

The compounds of the invention under consideration are centrally acting selective dopamine autoreceptor stimulating agents, and thus of great clinical interest in the treatment of psychotic disorders such as schizophrenia and a number of other disease states such as tardive dyskinesia, Huntington's chorea, alcoholism and drug abuse, said psychotic disorders and other disease states possibly being associated with a pathological increase in central dopamine transmission.

Best mode of carrying out the invention

The compound (−)-trans-(4aS;10bS)-7-hydroxy-1,2,3,4,4a,5,6,10b-octahydrobenzo(f)quinoline and its salts, processes for preparing said compound and methods of employing said compound in therapy, in particular for treatment of schizophrenia represents the best mode of carrying out the invention known to the inventors at present.

We claim:

1. A compound of the formula

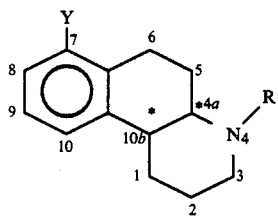

wherein $C^1$ and $N^4$ are in trans configuration to each other, Y is OH, $R^1COO$—, $R^2R^3NCOO$— or $R^4O$ whereby $R^1$ is an aliphatic hydrocarbon residue having 1-17 carbon atoms, a phenyl, 2,6-dimethylphenyl or 3- or 4-hydroxyphenyl group or a 3- or 4-alkanoyloxyphenyl group with the formula

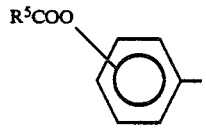

wherein $R^5$ is an alkyl group having 1-6 carbon atoms, or $R^1$ is a group

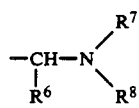

wherein $R^6$ is hydrogen, an alkyl group having 1 to 5 carbon atoms or a phenyl group, $R^7$ is hydrogen, an alkyl group having 1 to 5 carbon atoms or an acyl group having 2 to 7 carbon atoms and $R^8$ is hydrogen or an alkyl group having 1 to 5 carbon atoms, $R^2$ is hydrogen or an alkyl group having 1 to 5 carbon atoms, a phenethyl, benzyl or phenyl group which may be mono- or disubstituted in the aromatic part with a methyl, methoxy, hydroxy, nitro or cyano group or a halogen, $R^3$ is H, an alkyl group having 1 to 5 carbon atoms or a phenyl group and $R^4$ is an allyl or benzyl group, and R is hydrogen or the group

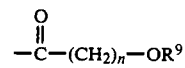

wherein n is 3 or 4 and $R^9$ is hydrogen, an alkanoyl group having 2-6 carbon atoms or benzoyl, as the base or a pharmaceutically acceptable acid addition salt thereof.

2. A compound according to claim 1, characterized in that Y is OH, $R^1COO$— or $R^2R^3NCOO$—, whereby $R^1$ is an alkyl group having 1-5 carbon atoms, or phenyl group, $R^2$ is an alkyl group having 1-5 carbon atoms, a phenethyl, benzyl or a phenyl group and $R_3$ is H or an alkyl group having 1-5 carbon atoms.

3. A compound according to claim 1, characterized in that Y is OH or $R^2R^3NCOO$—.

4. A compound according to claim 1, characterized in that R is hydrogen or 4-hydroxybutyryl.

5. A compound according to claim 1, characterized in that Y is OH and R is hydrogen or 4-hydroxybutyryl.

6. A compound according to claim 1, characterized by 4aS, 10bS configuration.

7. A pharmaceutical preparation comprising as an active ingredient a compound according to claim 1, in connection with a pharmaceutically acceptable carrier, the proportion of said active ingredient in said preparation being sufficient that the preparation is effective to evoke selective dopamine autoreceptor stimulation.

8. A method of inducing selective dopamine autoreceptor stimulation in patients wherein such stimulation is desired comprising administering a compound of the formula

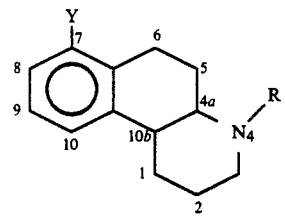

wherein
$C^1$ and $N^4$ are in trans configuration to each other,
Y is OH, $R^1COO$, $R^2R^3NCOO$— or $R^4O$
whereby $R^1$ is an aliphatic hydrocarbon residue having 1-17 carbon atoms, a phenyl, 2,6-dimethylphenyl or 3- or 4-hydroxyphenyl group or a 3- or 4-alkanoyloxyphenyl group with the formula

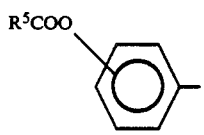

wherein $R^5$ is an alkyl group having 1-6 carbon atoms, or $R^1$ is a group

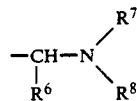

wherein R[6] is hydrogen, an alkyl group having 1 to 5 carbon atoms or a phenyl group, R[7] is hydrogen, an alkyl group having 1 to 5 carbon atoms or an acyl group having 2 to 7 carbon atoms and R[8] is hydrogen or an alkyl group having 1 to 5 carbon atoms, $R^2$ is hydrogen or an alkyl group having 1 to 5 carbon atoms, a phenethyl, benzyl or phenyl group which may be mono- or disubstituted in the aromatic part with a methyl, methoxy, hydroxy, nitro or cyano group or a halogen, $R^3$ is H, an alkyl group having 1 to 5 carbon atoms or a phenyl group, and $R^4$ is an allyl or benzyl group, and R is hydrogen or the group

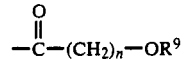

wherein n is 3 or 4 and $R^9$ is hydrogen, an alkanoyl group having 2-6 carbon atoms or benzoyl, or the base or a pharmaceutically acceptable acid addition salt thereof, said compound being administered in an amount effective to evoke selective dopamine autoreceptor stimulation.

* * * * *